United States Patent
Hessler et al.

(10) Patent No.: US 11,382,620 B2
(45) Date of Patent: Jul. 12, 2022

(54) STAPLE CARTRIDGE ASSEMBLY FOR USE IN A SURGICAL ROBOTIC SYSTEM

(71) Applicant: Covidien LP, Mansfield, MA (US)

(72) Inventors: Thomas Hessler, Bethel, CT (US); Anthony Calderoni, Bristol, CT (US); David Jermine, North Haven, CT (US)

(73) Assignee: Covidien LP, Mansfield, MA (US)

( * ) Notice: Subject to any disclaimer, the term of this patent is extended or adjusted under 35 U.S.C. 154(b) by 99 days.

(21) Appl. No.: 17/049,088

(22) PCT Filed: Apr. 1, 2019

(86) PCT No.: PCT/US2019/025124
§ 371 (c)(1),
(2) Date: Oct. 20, 2020

(87) PCT Pub. No.: WO2019/209467
PCT Pub. Date: Oct. 31, 2019

(65) Prior Publication Data
US 2021/0236123 A1    Aug. 5, 2021

Related U.S. Application Data

(60) Provisional application No. 62/661,333, filed on Apr. 23, 2018.

(51) Int. Cl.
*A61B 17/072* (2006.01)
*A61B 34/30* (2016.01)
(Continued)

(52) U.S. Cl.
CPC ............ *A61B 17/072* (2013.01); *A61B 34/30* (2016.02); *A61B 90/03* (2016.02); *A61B 90/96* (2016.02);
(Continued)

(58) Field of Classification Search
CPC ....... A61B 17/072; A61B 34/30; A61B 90/03; A61B 90/96; A61B 90/98
See application file for complete search history.

(56) References Cited

U.S. PATENT DOCUMENTS

2011/0288573 A1    11/2011  Yates et al.
2012/0085808 A1*   4/2012  Ehrenfels ............. A61B 17/105
                                                      227/180.1
(Continued)

FOREIGN PATENT DOCUMENTS

EP          3061404 A1      8/2016
JP       2004531280 A      10/2004
(Continued)

OTHER PUBLICATIONS

International Search Report dated Aug. 13, 2019, issued in corresponding international application No. PCT/US2019/025124, 6 pages.
(Continued)

*Primary Examiner* — Nathaniel C Chukwurah

(57) ABSTRACT

An end effector assembly for use in a surgical robotic system includes an anvil assembly and a staple cartridge assembly operably coupled to the anvil assembly. The staple cartridge assembly includes a chassis defining an elongate channel therein, a staple cartridge body configured for removable receipt in the elongate channel of the chassis, and a shipping wedge removably coupled to the staple cartridge body and at least partially covering a tissue-contacting surface of the staple cartridge body. The shipping wedge has a machine-readable medium thereon that stores a characteristic of the staple cartridge body.

11 Claims, 4 Drawing Sheets

(51) Int. Cl.
*A61B 90/96* (2016.01)
*A61B 90/00* (2016.01)
*A61B 90/98* (2016.01)

(52) U.S. Cl.
CPC .... *A61B 90/98* (2016.02); *A61B 2017/07257* (2013.01); *A61B 2017/07271* (2013.01); *A61B 2090/038* (2016.02)

(56) References Cited

U.S. PATENT DOCUMENTS

| | | | | |
|---|---|---|---|---|
| 2014/0252065 | A1* | 9/2014 | Hessler | A61B 17/072 227/176.1 |
| 2015/0324317 | A1* | 11/2015 | Collins | G06F 13/4221 710/106 |
| 2015/0351765 | A1* | 12/2015 | Valentine | G06F 11/1448 227/176.1 |
| 2016/0066915 | A1 | 3/2016 | Baber et al. | |
| 2016/0249921 | A1* | 9/2016 | Cappola | A61B 90/98 227/175.1 |
| 2017/0055981 | A1 | 3/2017 | Vendely et al. | |
| 2017/0265864 | A1 | 9/2017 | Hessler et al. | |
| 2017/0296190 | A1 | 10/2017 | Aronhalt et al. | |
| 2018/0085120 | A1 | 3/2018 | Viola | |

FOREIGN PATENT DOCUMENTS

| | | |
|---|---|---|
| JP | 2012196435 A | 10/2012 |
| JP | 2014171866 A | 9/2014 |
| JP | 2015231525 A | 12/2015 |
| JP | 2016528010 A | 9/2016 |
| KR | 101444058 B1 | 9/2014 |
| WO | 2011156733 A2 | 12/2011 |

OTHER PUBLICATIONS

Indian Office Action dated Aug. 10, 2021, issued in corresponding Indian Appln. No. 202017040918, 6 pages.
Australian Examination Report dated Jul. 13, 2021, issued in corresponding AU Appln. No. 2019257573, 3 pages.
Australian Office Action dated Feb. 11, 2021, issued in corresponding Australian Appln. No. 2019257573, 4 pages.
European Search Report dated Dec. 10, 2021, issued in corresponding EP Appln. 19792097, 10 pages.
Japanese Office Action dated Sep. 7, 2021, issued in corresponding JP Appln. No. 2020-554545, 6 pages.

* cited by examiner

STAPLE CARTRIDGE ASSEMBLY FOR USE IN A SURGICAL ROBOTIC SYSTEM

BACKGROUND

Surgical robotic systems have been used in minimally invasive medical procedures. Some surgical robotic systems included a console supporting a surgical robotic arm and a surgical instrument having at least one end effector (e.g., forceps or a grasping tool) mounted to the robotic arm. The robotic arm provided mechanical power to the surgical instrument for its operation and movement.

Manually-operated surgical instruments often included a handle assembly for actuating the functions of the surgical instrument. However, when using a robotic surgical system, no handle assembly was typically present to actuate the functions of the end effector. Accordingly, to use each unique surgical instrument with a robotic surgical system, an instrument drive unit was used to interface with the selected surgical instrument to drive operations of the surgical instrument.

The instrument drive unit was typically coupled to the robotic arm via a slide. The slide allowed the instrument drive unit and the attached surgical instrument to move along an axis of the slide, providing a means for adjusting the axial position of the end effector of the surgical instrument.

In some robotic systems, the end effector of the surgical instrument included a first jaw supporting an anvil assembly and a second jaw supporting a cartridge assembly. The cartridge assembly was often replaceable to permit reuse of the end effector during a surgical procedure. The replaceable cartridge assembly may have been provided in a variety of configurations for use on tissue having different properties, e.g., thickness, density, etc. For example, the different cartridge assemblies may have had staples of different sizes and/or the staples may be arranged in different configurations. The surgical robotic system required an update of its operating parameters to conform to the specifications of the particular cartridge assembly selected for use.

SUMMARY

In accordance with an aspect of the present disclosure, an end effector assembly for use in a surgical robotic system includes an anvil assembly and a staple cartridge assembly operably coupled to the anvil assembly. The staple cartridge assembly includes a chassis defining an elongate channel therein, a staple cartridge body configured for removable receipt in the elongate channel of the chassis, and a shipping wedge removably coupled to the staple cartridge body. The shipping wedge at least partially covers a tissue-contacting surface of the staple cartridge body and has a machine-readable medium thereon storing a characteristic of the staple cartridge body.

In aspects, the machine-readable medium may include barcodes, near-field communication tags, radio frequency identification device tags, and/or quick response codes.

In further aspects, the machine-readable medium may be printed on the shipping wedge.

In other aspects, the characteristic of the staple cartridge body may include a serial number of the staple cartridge body, a length of the staple cartridge body, or a reorder code.

In aspects, the shipping wedge may include a raised portion extending from a proximal end portion thereof configured to prevent approximation of the cartridge assembly towards the anvil assembly.

In some aspects, the shipping wedge may include a projection extending from a distal end thereof positioned and configured to be grasped by a clinician to facilitate separation of the shipping wedge from the cartridge assembly.

In other aspects, the shipping wedge may include a plurality of tabs configured to engage the staple cartridge body to releasably secure the shipping wedge to the staple cartridge body.

In another aspect of the present disclosure, a method of using an end effector assembly in a robotic surgical procedure is provided. A staple cartridge body of a staple cartridge assembly is loaded into an elongate channel defined in a chassis of the staple cartridge assembly. A shipping wedge at least partially covers a tissue-contacting surface of the staple cartridge body and is removably coupled to the staple cartridge body. A machine-readable medium disposed on the shipping wedge is scanned to identify a characteristic of the staple cartridge body, and the staple cartridge body is fired.

Some methods may further include disabling another firing of the staple cartridge body.

Some methods may further include removing the staple cartridge body from the chassis and loading another staple cartridge body into the elongate channel of the chassis. Another shipping wedge at least partially covers a tissue-contacting surface of the another staple cartridge body and is removably coupled thereto. The another shipping wedge has a machine-readable medium thereon storing a characteristic of the another staple cartridge body.

Some methods may further include scanning the machine-readable medium disposed on the another shipping wedge to identify a characteristic of the another staple cartridge body, and firing the another staple cartridge body.

Further details and aspects of exemplary embodiments of the present disclosure are described in more detail below with reference to the appended figures.

As used herein, the terms parallel and perpendicular are understood to include relative configurations that are substantially parallel and substantially perpendicular up to about + or −10 degrees from true parallel and true perpendicular.

BRIEF DESCRIPTION OF THE DRAWINGS

Embodiments of the present disclosure are described herein with reference to the accompanying drawings, wherein.

DETAILED DESCRIPTION

Figure 1:
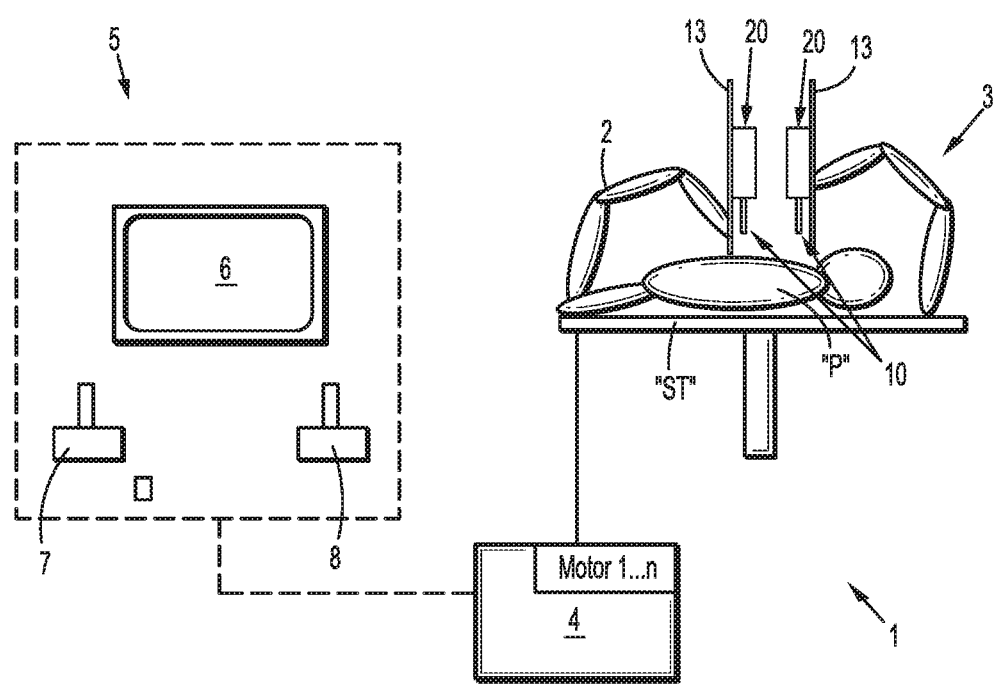
FIG. 1 is a schematic illustration of a surgical robotic system including a surgical instrument in accordance with the present disclosure.

Embodiments of the presently disclosed surgical robotic system and surgical instruments thereof are described in detail with reference to the drawings, in which like reference numerals designate identical or corresponding elements in each of the several views. As used herein, the term "distal" refers to that portion of the surgical robotic system or component thereof that is closest to the patient, while the term "proximal" refers to that portion of the surgical robotic system or component thereof further from the patient.

As will be described in detail below, provided is an end effector assembly for use in a surgical robotic system. The end effector assembly includes a staple cartridge body having a shipping wedge detachably coupled thereto. The shipping wedge is configured to prevent an approximation and/or firing of the end effector assembly until being removed from the staple cartridge body. The shipping wedge has a machine-readable medium (e.g., a barcode, an RFID tag, or a NFC tag) printed thereon. The machine-readable medium stores an identity of the staple cartridge body to allow the surgical robotic system to set the parameters required to operate the particular type of staple cartridge body selected for use. Other features and benefits of the disclosed end effector assemblies are further detailed below.

Referring initially to FIG. 1, a surgical system, such as, for example, a surgical robotic system 1, generally includes a plurality of surgical robotic arms 2, 3; an elongated slide 13 coupled to an end of each of the robotic arms 2, 3; an instrument drive unit 20 removably attached to the slide 13 and configured to move along the slide 13; an electromechanical surgical instrument 10 operably coupled to the instrument drive unit 20 and having an end effector assembly 100 (FIGS. 2-4); a control device 4; and an operating console 5 coupled with control device 4. The operating console 5 includes a display device 6, which is set up in particular to display three-dimensional images; and manual input devices 7, 8, by means of which a person (not shown), for example a surgeon, is able to telemanipulate robotic arms 2, 3 in a first operating mode, as known in principle to a person skilled in the art.

Each of the robotic arms 2, 3 may be composed of a plurality of members, which are connected through joints. Robotic arms 2, 3 may be driven by electric drives (not shown) that are connected to control device 4. Control device 4 (e.g., a computer) is set up to activate the drives, in particular by means of a computer program, in such a way that robotic arms 2, 3, the attached instrument drive units 20, and thus electromechanical instrument 10 execute a desired movement according to a movement defined by means of manual input devices 7, 8. Control device 4 may also be set up in such a way that it regulates the movement of the instrument drive unit 20 along the slide 13, movement of the robotic arms 2, 3, and/or movement of the drives.

Figure 2:
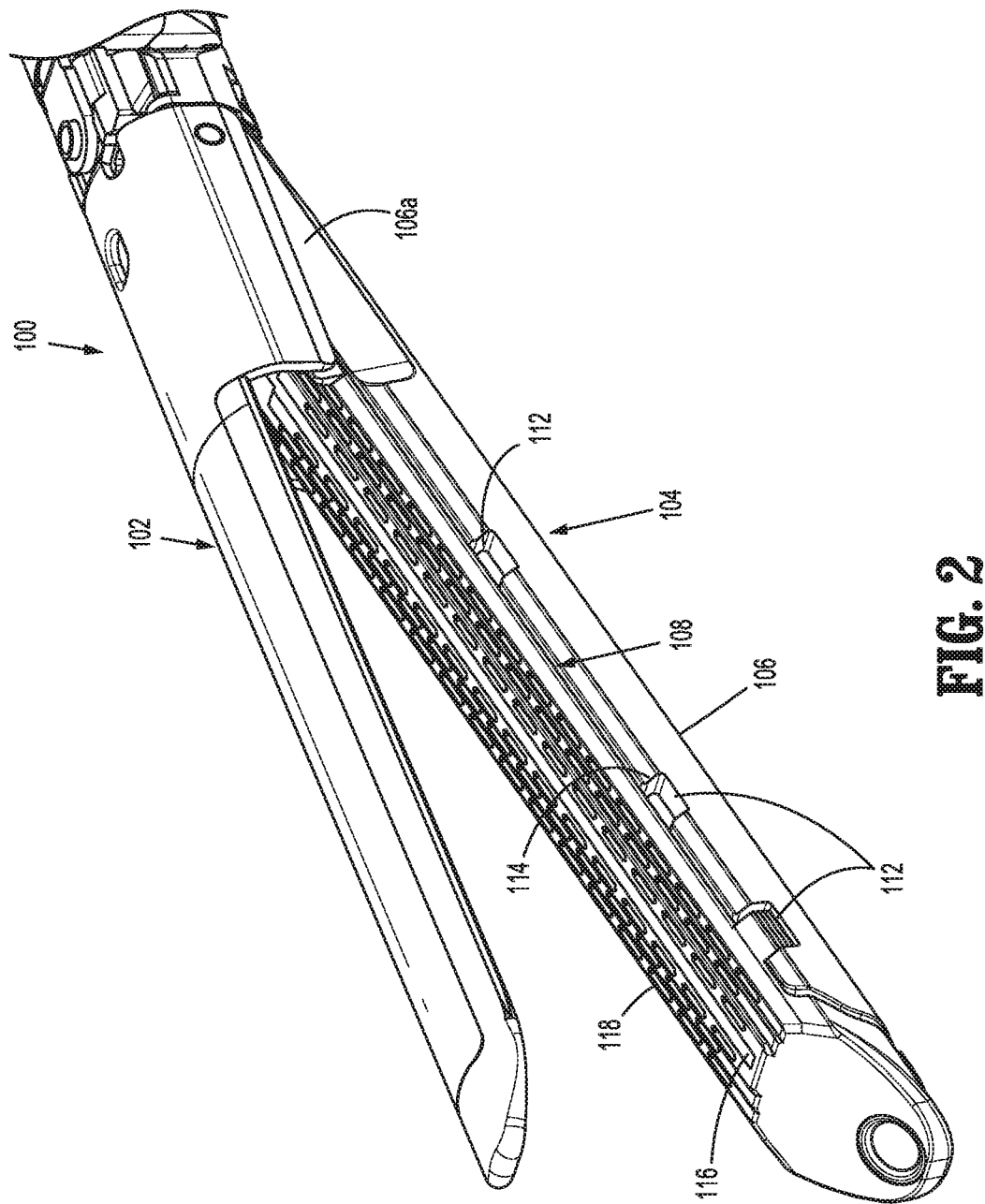
FIG. 2 is a side, perspective view of an end effector assembly of the surgical instrument shown in FIG. 1.
Figure 3:
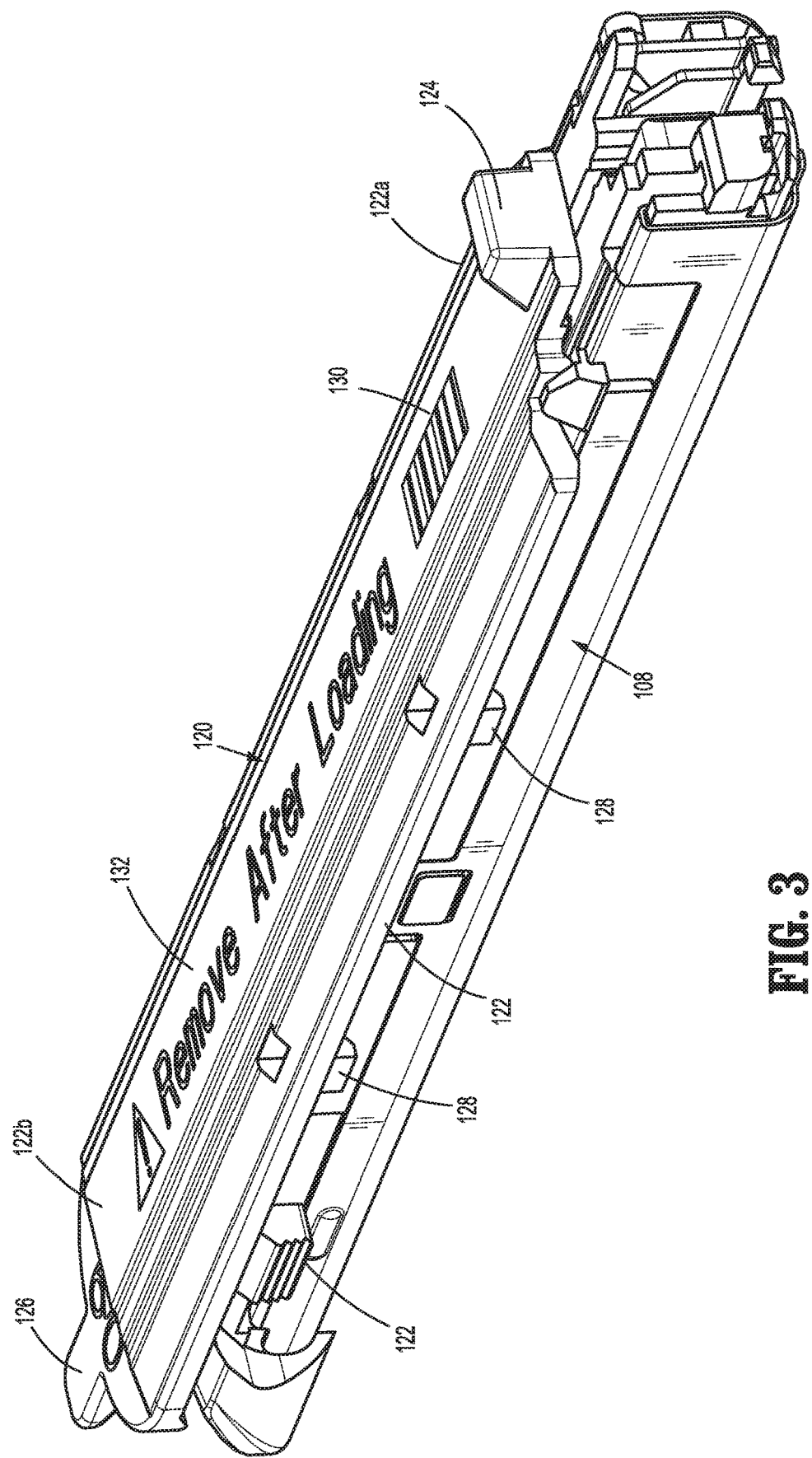
FIG. 3 is a rear, perspective view of a staple cartridge assembly of the end effector assembly of FIG. 2, including a staple cartridge body and a shipping wedge.
Figure 4:
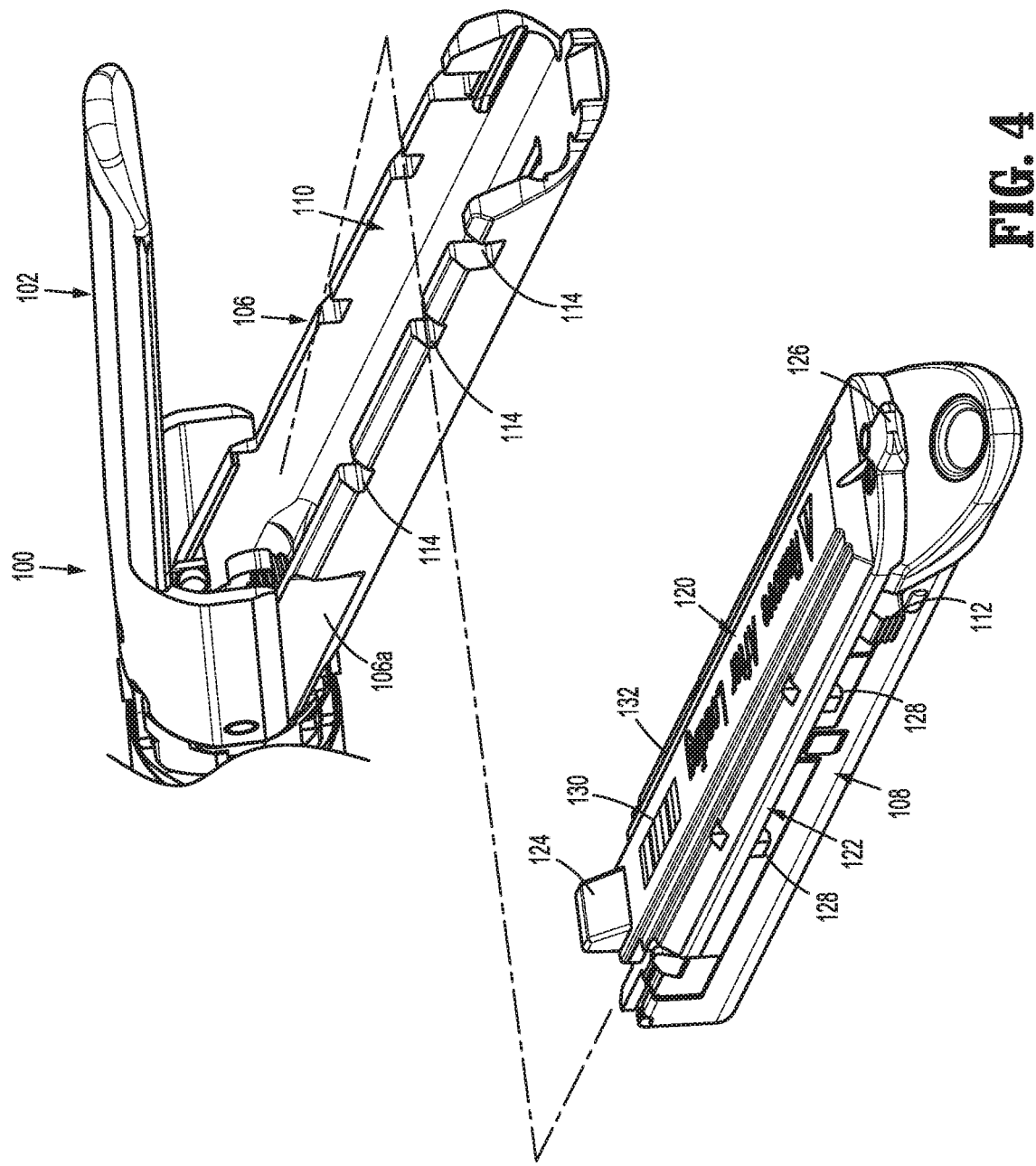
FIG. 4 is a rear, perspective view of the staple cartridge body and shipping wedge of FIG. 3 being loaded into a chassis of the staple cartridge assembly.

Surgical robotic system 1 is configured for use on a patient "P" lying on a surgical table "ST" to be treated in a minimally invasive manner by means of a surgical instrument, e.g., electromechanical instrument 10 having the end effector assembly 100 (FIGS. 2-4). Surgical robotic system 1 may also include more than two robotic arms 2, 3, the additional robotic arms likewise being connected to control device 4 and being telemanipulatable by means of operating console 5. A surgical instrument, for example, electromechanical surgical instrument 10 (including the electromechanical end effector assembly 100), may also be attached to the additional robotic arm.

Control device 4 may control a plurality of motors, e.g., motors (Motor 1 . . . n), with each motor configured to drive movement of robotic arms 2, 3 in a plurality of directions. Further, control device 4 may control a plurality of drive motors (not shown) of the instrument drive unit 20 to drive various operations of the surgical instrument 10. The instrument drive unit 20 transfers power and actuation forces from its motors to driven members (not shown) of the electromechanical instrument 10 to ultimately drive movement of components of the end effector assembly 100 of the electromechanical instrument 10, for example, a movement of a knife blade (not shown) and/or a closing and opening of jaw members 102, 104 (FIGS. 2-4) of the end effector assembly 100.

For a detailed description of the construction and operation of a robotic surgical system, reference may be made to U.S. Pat. No. 8,828,023, entitled "Medical Workstation," the entire contents of which are incorporated by reference herein.

With reference to FIGS. 2-4, an exemplary embodiment of an end effector assembly 100 of a surgical instrument 10 (FIG. 1) for use with the surgical robotic system 1 will now be described in detail. Although the end effector assembly 100 is shown and described as being operable by the surgical robotic system 1 (FIG. 1), it is envisioned that the end effector assembly 100 may also be operably coupled to a handle assembly of a powered, hand-held surgical stapling device.

The end effector assembly 100 of the surgical instrument 10 includes a first jaw member, such as, for example, an anvil assembly 102, and a second jaw member, such as, for example, a staple cartridge assembly 104, which are movable in relation to each other between approximated and expanded configurations. The end effector assembly 100 may be directly or indirectly coupled to a shaft portion (not shown) of the surgical instrument 10. The cartridge assembly 104 generally includes a chassis or staple cartridge receiving channel 106 and a disposable staple cartridge body 108 configured for removable receipt in the chassis 106. The chassis 106 has a proximal end portion 106a pivotably coupled to a proximal end portion of the anvil assembly 102. In embodiments, the proximal end portion 106a of the chassis 106 may be indirectly pivotably coupled to the anvil assembly 102. The chassis 106 defines an elongate channel 110 therein dimensioned for removable receipt of the staple cartridge body 108.

The staple cartridge body 108 has a plurality of tabs 112 extending from opposing lateral sides thereof. The tabs 112 of the staple cartridge body 108 are configured for a snap-fit connection in notches 114 defined in opposing lateral sides of the chassis 106. Other forms of connection are contemplated and can be used in place of the snap-fit connection or in addition thereto. The staple cartridge body 108 has a tissue-contacting surface 116 defining a plurality of rows of staple-retaining slots 118. The staple cartridge body 108 supports a plurality of staples (not shown) therein and is configured to discharge the staples through a respective staple-retaining slot 118 in the tissue-contacting surface 116.

With reference to FIGS. 3 and 4, the staple cartridge assembly 104 further includes a shipping wedge 120 configured to maintain the staples within the staple-retaining slots 118 of the tissue-contacting surface 116 of the staple cartridge body 108 and prevent actuation of the end effector assembly 100 prior to removal of the shipping wedge 120. The shipping wedge 120 includes an elongate body 122 dimensioned to cover the tissue-contacting surface 116 of the staple cartridge body 108. The elongate body 122 has a proximal end portion 122a covering a proximal end portion of the staple cartridge body 108, and a distal end portion 122b covering a distal end portion of the staple cartridge body 108.

The proximal end portion 122a of the elongate body 122 of the shipping wedge 120 has a raised portion 124 configured to prevent approximation of the cartridge assembly 104 towards the anvil assembly 102 once the staple cartridge body 108 is loaded within the channel 110 of the chassis 106 and prior to removal of the shipping wedge 120. The distal end portion 122*b* of the elongate body 122 has a projection 126 positioned and configured to be grasped by a clinician to facilitate separation of the shipping wedge 120 from the staple cartridge body 108. The elongate body 122 further includes a plurality of tabs 128 extending laterally from opposing lateral sides of the elongate body 122 for engaging the staple cartridge body 108 to releasably secure the shipping wedge 120 to the staple cartridge body 108.

The shipping wedge 120 has a machine-readable medium 130 printed on an upper surface 132 thereof. The machine-readable medium 130 may be a barcode, a near-field communication ("NFC") tag, a radio frequency identification device ("RFID") tag, a quick response code ("QR code"), a Bluetooth tag, or any other suitable machine-readable medium. The machine-readable medium 130 may be printed on, embedded in, or coated on the upper surface 132 of the shipping wedge 120 or any other suitable location of the shipping wedge 120. The machine-readable medium 130 stores a characteristic of the staple cartridge body 108, such as, for example, cartridge length, reorder number, staple arrangement, staple length, clamp-up distance, production date, model number, lot number, expiration date, etc.

A scanning device (not shown), such as a barcode reader, an RIFD reader, etc., may be used to read the information stored in the machine-readable medium 130 and transfer the information to the control device 4 (FIG. 1) of the surgical robotic system 1. In this way, upon the control device 4 (FIG. 1) receiving the information relating to the staple cartridge body 108, firing forces, the length of a firing stroke of the surgical instrument 10, etc., may be adjusted to accommodate the particular staple cartridge body 108. The control device 4 may be further configured prevent reuse of an empty or partially fired staple cartridge body 108 by requiring the detection of another machine-readable medium of another shipping wedge prior to enabling another firing of the end effector assembly 100.

In operation, a particular staple cartridge body 108 is selected depending on the type of surgical procedure to be performed, and is loaded into channel 110 of the chassis 106 of the staple cartridge assembly 104. A clinician or a robotic apparatus uses a reader to scan the machine-readable medium 130 on the shipping wedge 120 of the staple cartridge body 108 to identify a characteristic or a set of characteristics of the staple cartridge body 108, such as, for example, the length of the staple cartridge body 108. The identified characteristic of the staple cartridge body 108 is relayed to and recorded/stored in a look-up table or register of the control device 4 of the surgical robotic system 1, which control device 4 may then set the appropriate system parameters to ensure a proper use of the selected staple cartridge body 108. After the appropriate system parameters are set, the staple cartridge body 108 may be fired.

After firing of the staple cartridge body 108, the control device 4 disables any further firing of the partially or fully fired (e.g., used or spent) staple cartridge body 108, by assigning the recorded information of the staple cartridge body 108 to a "used" or "spent" storage table or registry of control device 4, necessitating the replacement of the used staple cartridge body 108 prior to executing another usage of the surgical instrument 10. The used staple cartridge body 108 may be removed from the chassis 106 and a new staple cartridge body (not shown) may then be loaded into the channel 110 of the chassis 110. A clinician or a robotic apparatus uses a reader to scan a machine-readable medium on a shipping wedge of the new staple cartridge body to identify a characteristic or a set of characteristics of the new staple cartridge body, such as, for example, the length of the new staple cartridge body. The identified characteristic or characteristics of the new staple cartridge body is relayed to the control device 4 of the surgical robotic system 1, which may then compare this information against the "used" or "spent" storage table or registry, to confirm that the loaded staple cartridge body is in-fact "new" (e.g., not used or spent), and adapt the system parameters to the requirements of the new staple cartridge body. In addition, once the machine-readable medium on the new staple cartridge body has been scanned and verified as new (e.g., not used or spent), the control device 4 of the surgical robotic system 1 may re-enable a firing of the new staple cartridge body.

In some embodiments, the chassis 106 of the staple cartridge assembly 104 may be equipped with a hermetically sealed switch (not shown), which is activated upon loading the staple cartridge body 108 into the chassis 106. For example, a sled (not shown) of the staple cartridge body 108, which is responsible for discharging the staples from the staple cartridge body 108, may contact the switch upon the staple cartridge body 108 being loaded into the chassis 106. The surgical robotic system 1 may use this mechanical interaction as a means of detecting the presence of the staple cartridge body 108. Further, upon advancement of the sled during staple firing, the switch may be deactivated, signaling to the surgical robotic system 1 that the staple cartridge body 108 has been used. The control device 4 may be programmed to disable any further firing of the staple cartridge body 108 after receiving a signal that the switch is deactivated.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

The invention claimed is:

1. An end effector assembly for use in a surgical robotic system, the end effector assembly comprising:
    an anvil assembly; and
    a staple cartridge assembly operably coupled to the anvil assembly, staple cartridge assembly including:
        a chassis defining an elongate channel therein;
        a staple cartridge body configured for removable receipt in the elongate channel of the chassis; and
        a shipping wedge removably coupled to the staple cartridge body and at least partially covering a tissue-contacting surface of the staple cartridge body, wherein the shipping wedge has a machine-readable medium disposed thereon storing a characteristic of the staple cartridge body.

2. The end effector assembly according to claim 1, wherein the machine-readable medium is selected from the group consisting of barcodes, near-field communication tags, radio frequency identification device tags, and quick response codes.

3. The end effector assembly according to claim 1, wherein the machine-readable medium is printed on the shipping wedge.

4. The end effector assembly according to claim 1, wherein the characteristic of the staple cartridge body includes at least one of a serial number of the staple cartridge body, a length of the staple cartridge body, or a reorder code.

5. The end effector assembly according to claim 1, wherein the shipping wedge includes a raised portion extending from a proximal end portion thereof configured to prevent approximation of the cartridge assembly towards the anvil assembly.

6. The end effector assembly according to claim 1, wherein the shipping wedge includes a projection extending from a distal end thereof positioned and configured to be grasped by a clinician to facilitate separation of the shipping wedge from the cartridge assembly.

7. The end effector assembly according to claim 1, wherein the shipping wedge includes a plurality of tabs configured to engage the staple cartridge body to releasably secure the shipping wedge to the staple cartridge body.

8. A method of using an end effector assembly in a robotic surgical procedure, the method comprising:
    loading a staple cartridge body of a staple cartridge assembly into an elongate channel defined in a chassis of the staple cartridge assembly, wherein a shipping wedge is removably coupled to the staple cartridge body and at least partially covering a tissue-contacting surface of the staple cartridge body;
    scanning a machine-readable medium disposed on the shipping wedge to identify a characteristic of the staple cartridge body; and
    firing the staple cartridge body.

9. The method according to claim 8, further comprising disabling another firing of the staple cartridge body.

10. The method according to claim 9, further comprising:
    removing the staple cartridge body from the chassis;
    loading another staple cartridge body into the elongate channel of the chassis, wherein another shipping wedge is removably coupled to the another staple cartridge body and at least partially covering a tissue-contacting surface of the another staple cartridge body, the another shipping wedge having a machine-readable medium disposed thereon storing a characteristic of the another staple cartridge body.

11. The method according to claim 10, further comprising:
    scanning the machine-readable medium disposed on the another shipping wedge to identify a characteristic of the another staple cartridge body; and
    firing the another staple cartridge body.

* * * * *